United States Patent [19]
Abel et al.

[11] Patent Number: 5,602,295
[45] Date of Patent: Feb. 11, 1997

[54] METHODS FOR THE ELIMINATION OF CYANIDES IN THE DEHALOGENATION OF HALOFLUOROCARBONS

[75] Inventors: Marc W. Abel, Columbus; Robert W. Mouk, Westerville; Alan F. Heyduk, Columbus; Albert E. Abel, Powell, all of Ohio

[73] Assignee: Commodore Laboratories, Inc., Columbus, Ohio

[21] Appl. No.: 435,781

[22] Filed: May 5, 1995

Related U.S. Application Data

[63] Continuation-in-part of Ser. No. 360,398, Dec. 21, 1994, Pat. No. 5,559,278, which is a continuation-in-part of Ser. No. 207,289, Mar. 7, 1994, Pat. No. 5,414,200.

[51] Int. Cl.$^6$ ............................................. A62D 3/00
[52] U.S. Cl. .................. 588/205; 588/207; 588/246; 570/262
[58] Field of Search .............................. 588/205, 207, 588/246; 423/DIG. 20; 570/262

[56] References Cited

U.S. PATENT DOCUMENTS

| | | | |
|---|---|---|---|
| 2,691,052 | 10/1957 | Cines | 260/648 |
| 3,004,075 | 10/1961 | Marcali | 260/648 |
| 4,341,641 | 7/1982 | Nuvak | 588/246 |
| 4,436,641 | 3/1984 | Stelz et al. | 252/68 |
| 4,732,609 | 3/1988 | Frey et al. | 588/246 |
| 5,110,367 | 5/1992 | Mazur et al. | 134/2 |
| 5,307,641 | 5/1994 | Kuoy | 62/59 |
| 5,414,200 | 5/1995 | Mouk et al. | 588/205 |

FOREIGN PATENT DOCUMENTS

| 59-10329 | 1/1984 | Japan | B01D 93/94 |
|---|---|---|---|

OTHER PUBLICATIONS

Ralph C Downing, Fluoro Carbon Refrigerawt Handbook Prentice Hall, pp. 177, 182–189, 302–303, 306–308 (1988).

*Primary Examiner*—Gary P. Straub
*Attorney, Agent, or Firm*—Howard M. Ellis

[57] ABSTRACT

Ozone depleting fluorocarbon compounds are dehalogenated through more economic reduction reaction with solvated electrons formed from lower equivalents of reactive metals than previously used by reacting the partial reduction products with nitrogen-containing bases, such as ammonia, or alternatively, without any reactive metal by reacting with the base alone. Mixtures of fluorocarbon refrigerants including difficult to separate azeotropes of dichlorodifluoromethane contaminated with chlorodifluoromethane are reclaimed by treating only with weak non-aqueous nitrogen-containing bases to provide essentially chemically pure dichlorodifluoromethane refrigerant suitable for recycling/reuse. Hazardous cyanides which may develop are converted to relatively benign products during the process by introducing a base to convert volatile cyanides to more stable salts which in turn are converted to useful compounds of lesser toxicity.

26 Claims, 1 Drawing Sheet

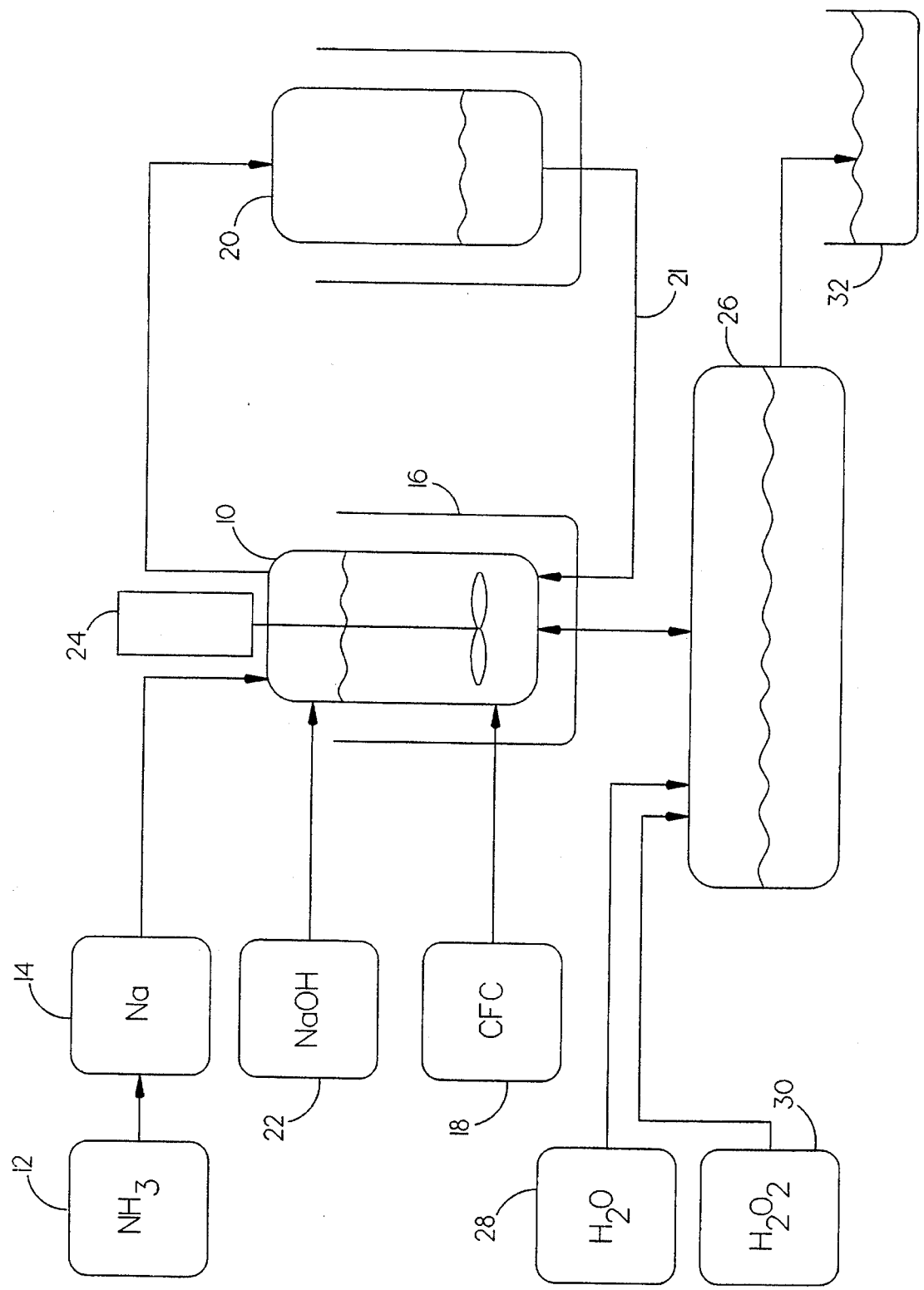

METHODS FOR THE ELIMINATION OF CYANIDES IN THE DEHALOGENATION OF HALOFLUOROCARBONS

CROSS-REFERENCE TO RELATED APPLICATION

This application is a continuation-in-part of application Ser. No. 08/360,398, filed Dec. 21, 1994, now U.S. Pat. No. 5,559,278, which is a continuation-in-part of application Ser. No. 08/207,289, filed Mar. 7, 1994 now U.S. Pat. No. 5,414,200.

TECHNICAL FIELD

The present invention relates generally to processes for destroying fluorocarbon compounds, and more specifically, to processes of dehalogenating environmentally harmful halofluorocarbons and halofluorohydrocarbons, e.g., CFCs, and potentially hazardous by-products which can form during the process.

BACKGROUND OF THE INVENTION

Chlorofluorocarbons (CFCs) are synthetic chemical compounds widely used in refrigeration and air conditioning; as aerosol propellants and solvents; in forming foams, including those used in fast-food packaging; and in rigid insulation. Scientists now view these synthetic chemicals as the main threat to Earth's protective ozone layer. Because CFCs are immune to destruction in the troposphere, and because they eventually float upwardly, their manufacture and release have lead to the accumulation of large amounts in the stratosphere. In the stratosphere, CFCs are broken down by sunlight into chlorine, which has a catalytic and destructive effect on ozone. The result has been a significant decline in the global ozone shield and an increase in the amount of harmful ultraviolet radiation reaching the surface of Earth. According to a United Nations' study, every 1 percent drop in ozone will lead to a 3 percent increase in non-melanoma skin cancers in light-skinned people, as well as dramatic increases in cataracts, lethal melanoma cancers, and damage to the human immune system. Higher levels of UV light may also worsen ground-level pollution and hurt plants, animals, and especially light sensitive aquatic organisms.

As a result, destruction of CFCs, and in some instances, reclamation of CFC refrigerants is a vital component of the national and global strategies for protection of the earth's ozone layer in a manner consistent with minimal economic disruptions associated with the phase-out of this class of chemicals. There are still sizable reserves of CFCs on hand which must be treated and converted to environmentally benign substances. Likewise, until existing refrigeration and air conditioning equipment is replaced or retrofitted with devices which are capable of operating with more environmentally friendly refrigerants, as CFC production is curtailed and eventually eliminated, industry and consumers must rely increasingly on the availability of reclaimed refrigerants.

Various methods have been proposed for the destruction of unwanted CFCs, such as thermal oxidation, catalytic decomposition, supercritical water oxidation, plasma destruction methods, biological processes, UV photolysis, to name but a few. Many are either in experimental stages of development, economically unattractive or incapable of selectively decomposing only specifically targeted compounds.

One other method for the destruction of CFCs is disclosed in U.S. Pat. No. 5,110,364 by Mazur et al, which provides for chemically degrading unwanted CFCs by dehalogenation reactions through solvated electron chemistry. Mazur et al disclose the formation of solvated electrons through dissolving metal reactions with nitrogen-containing bases, such as ammonia wherein chlorine atoms of the CFC compound are removed during the process to yield products having reduced environmental impact. A somewhat related process is also described in Japanese unexamined application 59-10329 (1984) to Showa Denko KK. Contrary to the disclosures of the earlier Showa Denko process, Mazur et al discovered the reduction of CFCs or other chlorinated organics, e.g. PCBs, with solvated electrons could be successfully carried out in the presence of substances previously thought to interfere with the stability of the solvated electrons or selectivity of the reaction. Mazur et al discovered the need for removing previously considered competing substances, such as oxygen, carbon dioxide, water, etc., from the reaction mixture was not required, and such costly pretreatment step(s) could be omitted.

Such earlier methods for the destruction of CFCs with solvated electrons may be demonstrated by the following representative reaction:

$$Cl_2F_2 + 8Na + 4NH_3 \rightarrow 2NaCl + 2NaF + CH_4 + 4NaNH_2$$

Sodium amide would then be converted to ammonia and sodium hydroxide as moisture becomes available as shown by the following equation:

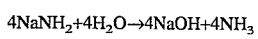
$$4NaNH_2 + 4H_2O \rightarrow 4NaOH + 4NH_3$$

While such reactions with solvated electrons provide a useful and practical solution for disposing of fluorocarbon compounds, including CFCs, in practice metal consumption and solvent requirements, e.g. sodium and ammonia are significant cost elements. Together, the two can make up as much as 70 percent of total operating costs. Of the two main reactants, ammonia is the far less costly, and processes for ammonia recovery are available. However, metals such as calcium, sodium and potassium are non-recoverable, and more costly consumable reactants which can detract from economics of the process.

Application Ser. No. 08/207,289, filed Mar. 7, 1994, now U.S. Pat. No. 5,414,200 by Robert W. Mouk and Albert E. Abel provides for an improved process based on the surprising observation that anhydrous liquid ammonia is a sufficiently strong base that it can react with and totally dehalogenate halofluorohydrocarbon refrigerants, like chlorodifluoromethane (Freon® 22) according to the following equation:

$$HCClF_2 + 5NH_3 \rightarrow NH_4Cl + 2NH_4F + NH_4CN$$

This reaction coupled with the surprising discovery that apparently complete destruction of halofluorocarbons can be accomplished with solvated electron solutions containing substantially less than stoichiometric amounts of metal led to the discovery that CFC destruction can be achieved by the following pathway:

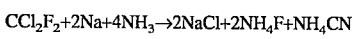
$$CCl_2F_2 + 2Na + 4NH_3 \rightarrow 2NaCl + 2NH_4F + NH_4CN$$

Although the Mouk et al process represents a significant advantage over earlier methods in that reactive metal consumption is effectively reduced by a factor of four, the process can nevertheless result in the formation of potentially hazardous ammonium cyanide.

Accordingly, it would be highly desirable to have a more improved process for the dehalogenation and destruction of fluorocarbons, and particularly CFCs, which allows for consumption of significantly reduced levels of metals and other reactants while also eliminating potentially hazardous by-products.

SUMMARY OF THE INVENTION

The term "refrigerant" as used throughout the specification and claims is a generic term intended to mean fluorocarbon compounds as a class of chemicals which are suitable for use in refrigeration and air conditioning equipment, but may have other applications. The term thus embraces halofluorocarbons and halofluorohydrocarbons, such as chlorofluorocarbons (CFCs), bromofluorocarbons, chlorofluorohydrocarbons, and so on. Likewise, the term "refrigerant" is also intended to include fluorocarbons which are useful as solvents, aerosol propellants, in manufacturing synthetic foams, packaging, insulation, retardant compounds for fire extinguishers, and the like. Thus, it should be understood the term "refrigerant" is intended to embrace a broader range of compounds than merely those which are suitable for air conditioning and refrigeration applications. They include products commercially available under trademarks, such as Freon, Halon, Frigen, Arcton, Genetron and Isotron.

In accordance with the invention an improved method is provided for dehalogenating refrigerants, and more particularly, fluorohydrocarbon refrigerants where instead of relying on the dissolution of a reactive metal in liquid ammonia or other nitrogen-containing base in the formation of solvated electrons, the improved method relies on the steps of:

(a) providing a fluoroalkane refrigerant having at least one hydrogen atom and at least one other halogen atom in addition to fluorine, and (b) in the absence of a dissolved metal reactant reacting the fluoroalkane refrigerant with only the nitrogen-containing base to dehalogenate and decompose the refrigerant. The nitrogen-containing base is non-aqueous.

Fluoroalkane as recited herein is intended to include halofluorohydrocarbons having in addition at least one hydrogen atom, at least one other halogen atom in addition to fluorine, i.e., chlorine, bromine and/or iodine. Fluoroalkane refrigerants are preferably intended to embrace halofluorohydrocarbons with <4 carbon atoms, and more preferably, compounds having 1 or 2 carbon atoms.

Unlike the foregoing method, U.S. Pat. No. 2,738,371 (Parmelee) provides for treating perfluorocarbons, i.e., compounds composed exclusively of 5 to 25 carbon atoms which are fully substituted with fluorine. Parmelee found that in the synthesis of perfluorocarbons, impurities develop consisting of incompletely fluorinated compounds containing up to 0.1 percent hydrogen. In reacting the impure perfluorocarbon composition with ammonia or an amine according to Parmelee's methods the fluorohydrocarbon is converted to fluorocarbon amine compounds.

In contrast, experimentation by the present inventors has shown that weak non-aqueous nitrogen-containing bases, like ammonia are capable of fully reacting with ozone depleting halofluorohydrocarbons, and particularly chlorofluorocarbons having 1 or 2 carbon atoms, such as chlorodifluoromethane to selectively dehalogenate and decompose them. Advantageously, it was also found that the environmentally harmful halofluorohydrocarbons can be eliminated without introducing metal into the reaction. In addition to more attractive economics of the process, any potential hazards associated with handling, transporting and storage of highly reactive alkali metals are avoided.

It is yet a further object of the invention to selectively dehalogenate compositions having a plurality of refrigerant compounds. Accordingly, the invention also contemplates reclamation methods wherein halofluorocarbon refrigerant which have become contaminated with halofluorohydrocarbon compounds are effectively purified. The method is carried out by the steps of:

(a) providing a composition with at least two refrigerants, (i) a primary perhalogenated compound and (ii) a contaminating fluoroalkane compound having at least one hydrogen atom and at least one other halogen atom in addition to fluorine;

(b) reacting the refrigerant composition of step (a) with a weak base, namely a non-aqueous nitrogen-containing compound, such as ammonia to selectively decompose the contaminating fluoroalkane refrigerant compound (ii), and (c) recovering a refrigerant composition from the reaction mixture of step (b), the composition comprising the primary perhalogenated refrigerant compound (i). The recovered composition is sufficiently free of the contaminating fluoroalkane refrigerant (ii) to enable recycling/reuse.

More preferably, the process comprises the steps of:

(a) providing a composition having at least two refrigerants, (i) a primary perhalogenated compound, usually a halofluorocarbon, e.g., chlorofluorocarbon, bromofluorocarbon, etc., and (ii) a contaminating fluoroalkane refrigerant compound having one or two carbon atoms, at least one hydrogen atom and at least one other halogen atom in addition to fluorine, e.g., chlorine, bromine or iodine;

(b) reacting the refrigerant composition of step (a) with a non-aqueous nitrogen-containing base to selectively decompose the contaminating fluoroalkane refrigerant compound (ii), and (c) recovering a refrigerant composition from the reaction mixture of step (b), the composition comprising the primary perhalogenated refrigerant compound (i), the recovered composition being sufficiently free of the contaminating fluoroalkane refrigerant compound (ii) to enable recycling/reuse.

This aspect of the invention is particularly unique in view of the discovery that weak nitrogen-containing bases are capable of selectively dehalogenating/decomposing halofluorohydrocarbons (ii) without also reacting with the primary fluorocarbon compounds (i). The selectivity of the process is also significant in permitting the recovery of refrigerants from mixtures which otherwise could not be readily purified through distillation methods because of their forming azeotropes with other refrigerants. Heretofore, such azeotropes were disposed of by decomposing the entire mixture since there was no practical and economic means for separation and recovery of the still useful refrigerant compounds.

It is still a further object of the invention to provide for an improved method of dehalogenating fluorocarbon refrigerants by a reduction mechanism through dissolving metal reaction in a nitrogen-containing base, such as ammonia. Unlike earlier methods for the destruction of unwanted ozone depleting perhalogenated refrigerants with solvated electrons which typically employed 8 equivalents of reactive metal per mole of refrigerant, the present inventors discovered that dehalogenation of such refrigerants could be effectively performed with only a fraction of the metal previously used, thereby making the process economically more attractive. The improved method includes the steps of:

(a) providing a perhalogenated fluorocarbon refrigerant having at least one other halogen atom in addition to fluorine, e.g., chlorine, bromine and iodine;

(b) forming a solution of solvated electrons by dissolving in ammonia or other weak nitrogen-containing base a substoichiometric amount of the reactive metal in an amount about sufficient to partially reduce the perhalogenated refrigerant of step (a) by removing one halogen atom therefrom;

(c) reacting the refrigerant of step (a) in the solution of solvated electrons of step (b), the reaction being conducted at temperatures sufficiently low as to retard reactions of the solvated electrons and liquid ammonia or other nitrogen-containing base with by-products of the reduction reaction, and (d) elevating the temperature of the reaction mixture of step (c) to initiate further dehalogenation by reacting with the ammonia or other nitrogen-containing base to form compounds which are non-ozone depleting.

The foregoing method is preferably performed by the steps of:

(a) providing a perhalogenated fluorocarbon refrigerant;

(b) forming a solution of solvated electrons by dissolving in the liquid ammonia or other nitrogen-containing base the reactive metal in an amount about sufficient to partially reduce the perhalogenated fluorocarbon refrigerant of step a;

(c) reacting the refrigerant of step (a) in the solution of solvated electrons of step (b), the reaction being conducted at temperatures sufficiently low as to retard reactions of the solvated electrons and liquid ammonia or other nitrogen-containing base with by-products of this reduction reaction, and (d) elevating the temperature of the reaction mixture of step (c) to initiate further dehalogenation by reacting with the liquid ammonia or other nitrogen-containing base.

It is yet a further object of the invention to provide an improved method for the dehalogenation of fluorocarbon refrigerants and the elimination of potentially hazardous cyanide compounds by the steps of:

(i) providing a halofluorohydrocarbon refrigerant;

(ii) reacting the halofluorohydrocarbon refrigerant with an ammonia or other nitrogen-containing base to dehalogenate the refrigerant, the reaction yielding a composition comprising a cyanide compound;

(iii) reacting the cyanide compound with a base selected from the group consisting of an alkali metal hydroxide and an alkaline earth metal hydroxide to provide a reaction mixture comprising a cyanide compound of the base, and (iv) hydrolyzing with water the cyanide compound of the base to yield a composition substantially free of the compound.

Halofluorohydrocarbon refrigerants are intended to include chlorofluorohydrocarbons and bromofluorohydrocarbons. Representative examples from the fluoromethane series include such members as chlorodifluoromethane, fluorodichloromethane, chlorofluoromethane, bromofluoromethane, bromodifluoromethane, mixtures of the same, and so on.

The foregoing improved methods for the dehalogenation of refrigerants and the elimination of hazardous cyanide compounds may also be employed in the purification of refrigerants contaminated with other unwanted refrigerants by the steps of:

(i) providing a composition comprising at least two refrigerants, (a) a primary perhalogenated refrigerant compound and (b) a contaminating halofluorohydrocarbon refrigerant compound;

(ii) reacting the refrigerant composition of step (i) with a nitrogen-containing base to selectively decompose the contaminating halofluorohydrocarbon refrigerant compound (b) and yield a composition comprising the primary perhalogenated refrigerant compound and a cyanide compound;

(iii) reacting the cyanide compound of step (ii) with a base selected from the group consisting of an alkali metal hydroxide and an alkaline earth metal hydroxide to yield a reaction mixture comprising the primary perhalogenated refrigerant and a cyanide compound of the base;

(iv) hydrolyzing with water the cyanide compound of the base of step (iii) to form a useful product or a product of lesser toxicity, and (v) recovering the primary perhalogenated refrigerant sufficiently free of the contaminating halofluorohydrocarbon refrigerant to enable recycling/reuse.

A primary perhalogenated refrigerant compound (a) of step (i) is a fully halogenated refrigerant compound, and includes such members as chlorofluorocarbons and bromofluorocarbons. A representative example includes dichlorodifluoromethane. The contaminating halofluorohydrocarbon refrigerant compounds (b) of step (i) typically include chlorofluorohydrocarbons and bromofluorohydrocarbons, such as fluoromethane types like chlorodifluoromethane, fluorodichloromethane, chlorofluoromethane, bromofluoromethane, bromodifluoromethane, and mixtures thereof. This method also contemplates purification of refrigerant mixtures which are present as azeotropes, or mixtures of at least two refrigerants having substantially similar boiling points.

It is still a further object of the invention to provide for the dehalogenation of perhalogenated refrigerant compounds with the elimination of hazardous cyanide compounds utilizing solvated electrons prepared with less than stoichiometric (substoichiometric) amounts of metal to partially dehalogenate the refrigerant and form a refrigerant carbanion. Dehalogenation of the carbanion is completed through the ammonia or other nitrogen-containing base solvent. The methods may be performed by the following steps:

(i) providing a perhalogenated fluorocarbon refrigerant;

(ii) forming a solution of solvated electrons by dissolving a reactive metal in a solvent carrier of liquid ammonia or other nitrogen-containing base, the reactive metal being present in an amount sufficient to only partially dehalogenate the perhalogenated refrigerant;

(iii) reacting the refrigerant of step (i) with the solution of solvated electrons of step (ii) to yield a composition comprising a partially dehalogenated refrigerant carbanion;

(iv) allowing the refrigerant carbanion and any subsequent intermediates to react with the solvent carrier to complete the dehalogenation of the refrigerant and yield a reaction mixture comprising a cyanide compound;

(v) reacting the cyanide-containing reaction mixture of step (iv) with a metal hydroxide base to yield a reaction mixture comprising a cyanide compound of the base;

(vi) hydrolyzing with water the cyanide compound of the base of step (v) to form a useful product or a product of lesser toxicity. The solvated electrons of step (ii) are formed from a reactive metal selected from the group consisting of an alkali metal, alkaline earth metal, aluminum and mixtures thereof, and the solvent carrier is usually anhydrous liquid ammonia.

The substoichiometric method may be illustrated by the following equations:

$$CCl_2F_2 + 2Na + 4NH_3 \rightarrow 2NaCl + 2NH_4F + NH_4CN$$

Any ammonium cyanides formed in the process are converted to alkali metal cyanides as illustrated below:

$$NH_4F + NaOH \rightarrow NaF + NH_3 + H_2O$$

$$NH_4CN + NaOH \rightarrow NaCN + NH_3 + H_2O$$

Ammonia can be recovered for recycling. Most preferably, the ammonia employed is anhydrous liquid ammonia, however, other nitrogen-containing bases may be used which are refrigerant soluble primary amines, secondary amines or tertiary amines.

The alkali metal cyanides are hydrolyzed to form useful products, such as sodium formate according to the reaction below:

$$NaCN + 2H_2O \rightarrow HCOONa + NH_3$$

Generally, the method is performed with a reactive metal present in a sufficient amount to remove at least one but fewer than all of the halogens on the perfluorocarbon refrigerant. This means the solvated electrons are formed with about 2 equivalents of reactive metal per mole of perhalogenated fluorocarbon refrigerant present rather than 8 equivalents with stoichiometric methods.

Reactions of step (iii) are conducted at temperatures sufficiently low as to retard reactions of the solvated electrons and anhydrous liquid ammonia with by-products of this reduction reaction.

Typical perhalogenated fluorocarbon refrigerants of step (i) are chlorofluorocarbons and bromofluorocarbons. Representative examples include chlorotrifluoromethane, bromotrifluoromethane, fluorotrichloromethane and dichlorodifluoromethane.

BRIEF DESCRIPTION OF THE DRAWING

The drawing is a schematic diagram for the process of combined dehalogenation of fluorocarbon refrigerants with solvated electrons and ammonia with the elimination of hazardous cyanide by-products

DESCRIPTION OF THE PREFERRED EMBODIMENTS

Methods of the invention include the dehalogenation and destruction of "fluoroalkane" refrigerants which term for purposes of this invention is intended to mean principally fluoromethane type refrigerants, but also fluoroethane types. The fluoroalkane refrigerants have at least one hydrogen atom and one other halogen atom in addition to fluorine, namely chlorine, bromine and/or iodine. Representative fluoroalkane types include refrigerants available under the E. I. dupont trademark Freon®, such as Freon 22 (chlorodifluoromethane), Freon 21 (fluorodichloromethane), Freon 31 (chlorofluoromethane), Freon 31B1 (bromofluoromethane), Freon 22B1 (bromodifluoromethane), and mixtures of the same. Other fluoroalkane refrigerants include, for instance, 1,1,2,2-tetrachloro-2-fluoroethane (FC-121); 1,1,1-trifluoro-2,2-dichloroethane (FC-123).

One preferred embodiment of the invention includes reacting the foregoing fluoroalkane refrigerants with a non-aqueous nitrogen-containing base. The expression "non-aqueous nitrogen-containing base", or similar variations thereof as appearing in the specification and claims is intended to mean substantially free of water. That is to say, the expression is intended to denote anhydrous bases which are free of any water, but also nitrogen-containing bases having small or minor amounts of water ranging from 3 percent or less, which may be present, for example, as an impurity.

Representative examples of non-aqueous nitrogen-containing bases include mainly ammonia, i.e. anhydrous liquid ammonia and liquid ammonia having minor amounts of water, i.e. 3 percent or less. Other suitable non-aqueous nitrogen-containing bases in addition to ammonia which may be employed in the dehalogenation of fluoroalkane refrigerants include primary amines, secondary amines, tertiary amines, cyclic amines, heterocyclic alkyl mono and polyamines and mixtures thereof. Representative examples of such bases include methyl amine, ethyl amine, dimethyl amine, diethyl amine, triethyl amine, n-propyl amine, piperidine, morpholine and ethylenediamine.

The foregoing nitrogen-containing bases are weak bases. For purposes of this invention the expression "weak base" is generally intended to encompass mainly nitrogen-containing bases having a $pK_b$ in the range of 2 to 5.

The non-aqueous nitrogen-containing bases are suitable for use as is, or they may be mixed with other organic solvents provided the solvents are substantially soluble in the refrigerant, and do not react with the base. Representative examples of suitable organic solvents include primary alcohols, such as methanol, ethanol, propanol, butanol; secondary alcohols like 2-propanol; ethers, such as diethyl ether and 1,4-dioxane; glycol monoethers like methoxyethanol and butoxypropanol; nitriles, such as acetonitrile, and amides like N,N-dimethylformamide or N,N-dimethylacetamide.

Dehalogenation of fluoroalkanes with non-aqueous nitrogen-containing bases is readily performed in a pressure vessel at ambient temperature conditions, which includes temperatures generally in the range of about 10° to about 70° C. The concentration of the nitrogen-containing base employed is generally in the range of about 10 percent to about 100 percent. The reactions are preferably conducted under anaerobic conditions. A means of removing insoluble reaction products (salts) by filtration is provided.

As a further preferred embodiment, the invention includes methods for selective dehalogenation of refrigerant compositions containing two or more refrigerants. More particularly, the invention includes methods for purification of refrigerant compositions containing useful primary refrigerants which have become contaminated with other refrigerants. Expressions like "primary refrigerant" and "primary perhalogenated refrigerant" as appearing herein are used to denote the specific refrigerant(s) desired for recovery from contaminated refrigerant mixtures in the dehalogenation process. Primary refrigerants include mainly refrigerants which are perhalogenated, or in other words, fluorocarbon refrigerants in which all the carbons are fully substituted with halogen atoms. They include such representative examples as Freon® 11 (fluorotrichloromethane), Freon 12 (dichlorodifluoromethane), Freon 13 (chlorotrifluoromethane), Freon 14 (tetrafluoromethane), Freon 13B1 (bromotrifluoromethane), and so on.

The expression "other refrigerant" is used herein to denote the contaminating or unwanted refrigerant portion to be eliminated from refrigerant compositions containing the primary refrigerant. Other refrigerants correspond to the "fluoroalkane refrigerants" previously discussed in connection with the first embodiment of the invention, and includes halofluorohydrocarbon compounds having <4 carbons, and more preferably 1 or 2 carbon atoms, at least one hydrogen atom and at least one other halogen atom in addition to fluorine, e.g. chlorine, bromine and/or iodine. Representative examples include chlorodifluoromethane, fluorodichloromethane, chlorofluoromethane, bromofluoromethane, bromodifluoromethane, and mixtures of the same.

This second embodiment of the invention is useful in reclaiming refrigerant compositions. In order to qualify for reuse, reclaimed refrigerants are required to meet the American Refrigeration Institute's "700" specifications which stipulate the permissible levels of contaminants. That is, strict limits are placed on moisture, particulates, acidity, oil content, non-condensible gases, and other refrigerants present. Existing reclamation processes are capable of meeting all of the foregoing criteria with the exception of "other refrigerants", which are not permitted to exceed 0.5 percent maximum.

Hence, the second embodiment of the invention is useful in treating mixtures of fluorocarbon compounds, including those contaminated with >0.5 percent of other refrigerant. However, methods of the present invention are also effective in treating compositions containing minor or even trace amounts, i.e., <0.5 percent other refrigerant(s). One representative example of a widely found refrigerant mixture is dichlorodifluoromethane also known as Freon® 12 or FC-12, which is frequently contaminated with Freon 22 or chlorodifluoromethane, both hereinafter called R-12 and R-22, respectively. Although removal of the unwanted R-22 contaminant from such a mixture would appear to be readily accomplished by distillation due to differences in their boiling points (R-12 b.p. −29.8° C. and R-22 b.p. −41° C.), separation by distillation is not readily achieved due to the formation of an azeotrope consisting of 75 percent R-22, when the two refrigerants become mixed.

The principal object of this embodiment of the invention is the selective chemical decomposition of other refrigerants in compositions of refrigerant mixtures without loss of the primary refrigerant. This includes the steps of separation and recovery of the composition containing the primary refrigerant from the reaction medium in a refined or purified state free or virtually free of other refrigerant, so as to meet ARI specifications for other refrigerants. The methods of this second embodiment are especially useful in recycling discontinued or potentially scarce refrigerant compounds.

While the methods of the invention are especially useful in the reclamation of contaminated perhalomethane type primary refrigerants the invention contemplates the purification and recovery of other perhaloalkane primary refrigerants as well, such as the fluoroethanes and fluorobutanes. Representative examples include fluorocarbon or FC-112 (1,1,2,2-tetrachloro-1,2-difluoroethane), FC-113 (1,1,2-trichloro-1,2,2-trifluoroethane), and the like.

In addition to the reclamation of refrigerant compositions comprising a single perhalogenated primary refrigerant contaminated with other refrigerant(s), the invention contemplates the purification of refrigerant mixtures having similar boiling points, and particularly azeotrope refrigerants, like Freon 500 (dichlorodifluoromethane and 2,2-difluoroethane), Freon-503 (trifluoromethane and chlorotrifluoromethane), and particularly an azeotrope of dichlorodifluoromethane in which the halofluorohydrocarbon, chlorodifluoromethane is the other refrigerant.

The reaction of the non-aqueous nitrogen-containing base with the contaminated refrigerant composition is performed in a closed pressure vessel at ambient temperature conditions. The process may be either batch or continuous. With amines of suitably high boiling point purified refrigerant may be separated from the reaction mixture by evaporation. However, with ammonia or low boiling amines the separation is accomplished by passing the vaporized mixture through water, dilute acid or a sequence of the two to selectively dissolve the amine either as the free base or as a salt thereof. The refrigerant vapors are then compressed and cooled to bring it to the liquid state.

As a third embodiment of the invention, fluorocarbon refrigerants, and particularly perhalogenated types which are not readily dehalogenated with weak bases, such as dichlorodifluoromethane, chlorotrifluoromethane, bromotrifluoromethane, and other perhalogenated fluorocarbons are partially dehalogenated initially through a reduction reaction with solutions of solvated electrons. It was found, this partial dehalogenation reaction of fluorocarbon refrigerants requires as little as one fourth of the reactive metal ordinarily employed in processes, such as disclosed by U.S. Pat. No. 5,110,364 and Japanese Unexamined Application 59-10329 (1984). Such prior methods provide for removal of all halogen atoms from the perhalomethane refrigerants with stoichiometric amounts of reactive metals, such as sodium in the formation of solvated electrons with ammonia or other nitrogen-containing solvent. Unlike earlier methods, the improved process of the immediate invention provides for the removal of as little as a single halogen atom, e.g., chlorine, bromine or iodine, thereby requiring but a fraction of the metal reactant, in view of the lesser requirement for solvated electrons. With the removal of as little as a single halogen atom, further dehalogenation of the fluorocarbon is achieved with the remaining available ammonia or other nitrogen-containing base in the reaction mixture.

While not wishing to be held to any specific mechanism of action relative to this third embodiment, it is nevertheless believed that partial reduction or dehalogenation of a perhalocarbon refrigerant by treating in a solution of solvated electrons might result in hydrogenating the starting refrigerant, and possibly form a halohydroalkane intermediate which is subject to further dehalogenation through acid-base reaction with the residual ammonia or other nitrogen-containing base remaining in the reaction mixture.

The solvated electrons are formed in a dissolving metal reaction with ammonia or other nitrogen-containing base, such as a fluorocarbon soluble primary amine, secondary amine or tertiary amine. Specific representative examples were previously provided. The reactive metals may consist of alkali metals, such as sodium, potassium and lithium, and alkaline earth metals, like calcium and magnesium. Mixtures of such metals may also be employed. Aluminum may also be used as a dissolving metal. Compared with the stoichiometric amounts of metal per mole of perfluorocarbon refrigerant employed according to earlier methods, the present invention utilizes 2 mole equivalents of reactive metal per mole of perhalogenated fluorocarbon, or in other words, one fourth of the amount of metal previously required.

Reduction of the perfluorocarbon refrigerant with solvated electrons is carried out in a closed pressure vessel at temperatures sufficiently low as to retard reactions which might otherwise occur between by-products of the reduction reaction and the solvated electrons or nitrogen-containing base. Typically, reactions would be conducted at about 0° C. or lower. Subsequently the reaction vessel is allowed to warm to ambient temperature which will in-turn initiate further dehalogenation of the partially dehalogenated fluorocarbon to completely dehalogenate it, i.e. remove the remaining fluorine, chlorine, bromine and/or iodine atoms as an acid-base reaction with residual ammonia or other nitrogen-containing base.

The present invention also contemplates the dehalogenation and destruction of CFCs while eliminating potentially hazardous by-products, like ammonium cyanide, which can develop. For example, in the case of dehalogenating perhalogenated fluorocarbon refrigerants, such as dichlorodifluoromethane (Freon-12 or R-12), the CFC is treated with two electrons (solvated) formed from a substoichiometric amount of metal dissolved in anhydrous liquid ammonia, for example, to effectuate removal of usually at least one halogen, e.g., chlorine, but fewer than all the halogen atoms from the CFC molecule. The refrigerant carbanion and any subsequent intermediates are further acted upon by the ammonia carrier solvent until the refrigerant carbanion is fully dehalogenated. Hazardous compounds, like ammonium cyanide, are converted to useful products or to products of lesser toxicity by reacting with a base, such as an alkali metal hydroxide, preferably sodium or potassium hydroxide, or an alkaline earth metal hydroxide, such as calcium hydroxide, to form alkali metal or alkaline earth metal cyanide intermediate which can be hydrolyzed with water to form the corresponding formate salt. Ammonia liberated in these reactions can be recovered for recycling.

This aspect of the invention can be further illustrated by referring to the accompanying flow diagram. The first two steps of the process are performed with liquid ammonia and dissolving metal, such as sodium metal being added to reactor vessel 10 forming a solvated electron solution. The dissolving metal can be added either as solid metal via a lock-hopper arrangement or as part of a metal-ammonia solution wherein ammonia from vessel 12 is fed to an in-line solvator 14 containing sodium or calcium metal. Reactor 10 is equipped with a jacket 16 and contains a heat transfer fluid, e.g. water, ethylene glycol. As the reaction exotherm adds energy to the system the heat transfer fluid functions in controlling temperature increases.

Liquid refrigerant stored in holding tank 18 is charged to the solution of solvated electrons in vessel 10. As the reaction takes place, the exotherm mentioned above is generated and the CFC is converted to sodium salts, ammonium salts and ammonium cyanide. Although the reaction products differ somewhat for CFC compounds containing more than one carbon atom, it is believed the general pathway for multiple carbon compounds is analogous to single carbon compounds.

When the reaction between the CFC and the solution of solvated electrons is complete, residual ammonia is removed from vessel 10 as a vapor and transferred to jacketed ammonia holding tank 20 where it is cooled to a liquid. Although small quantities of hydrogen cyanide and unreacted CFCs from the reactor headspace may transfer along with the ammonia this does not create a problem because they will be returned to vessel 10 when the ammonia is returned for treating subsequent batches of CFCs via line 21, and eventually be destroyed. The thermal mass of vessel 10 assists in driving the ammonia from that vessel to ammonia holding tank 20 and minimizes the requirement for supplemental heat vaporization.

Caustic soda solution from vessel 22 is added to vessel 10 and stirrer 24 actuated. The salts and cyanide compound are converted to sodium compounds, ammonia and water. Slurried sodium salts and sodium cyanide are transferred to hydrolyzer vessel 26 from vessel 10 where water is added to the mixture from holding tank 28. The mixture is then heated to about 100° F. until all the sodium cyanide has been converted to sodium formate and ammonia. Ammonia generated in the hydrolysis reaction is recycled for further use by returning to vessel 10. Ammonia from holding vessel 20 is returned to reaction vessel 10, where the foregoing process steps are repeated.

Although not likely to occur, in the event that trace amounts of residual cyanide remain in the reaction products, a small quantity of peroxide 30 can be added to vessel 26 to assure that no cyanide compound remains. Reaction by-products, e.g., sodium formate can be transferred to storage tank 32 pending disposal.

The following specific examples demonstrate the various embodiments of the invention, however, it is to be understood they are for illustrative purposes only and do not purport to be wholly definitive as to conditions and scope.

EXAMPLE I

In order to demonstrate that a nitrogen-containing base, such as ammonia was capable of effectively destroying halohydroalkane refrigerants in the absence of a dissolving metal reactant, such as sodium or calcium, an initial experiment was conducted using a reactor consisting of an Ace Glass, Inc., heavy walled threaded glass tube fitted with a Teflon® stopper and pressure gauge. The tube was charged with 25.0 g of anhydrous liquid ammonia (1.5 moles) and 4.1 g of pure chlorodifluoromethane refrigerant (R-22). The tube was charged while being cooled in dry ice/isopropyl alcohol (IPA). Once charging was completed the tube was sealed and allowed to warm to room temperature. Within 80 minutes after mixing the reactants, salt crystals were observed at the bottom of the tube consisting of by-products of the reaction. Additional salts were observed to be continually forming. Within 140 minutes into the experiment the reaction was judged to be complete and the reactor tube was again cooled in dry ice/IPA to reduce pressure in the tube from the ammonia. The pressure gauge was replaced with a stopper vented through a Teflon tube, and the reaction tube was allowed to warm. When gas evolution ceased 7.5 g of solids were recovered. The stoichiometric yield of products was 8.1 g, indicating at least 93 percent of the R-22 was destroyed in the reaction.

EXAMPLE II

In order to demonstrate the selectivity of weak nitrogen-containing bases in the absence of a dissolving metal, such as potassium or calcium, in the purification of refrigerant mixtures a further experiment was conducted. 90.5 g of a refrigerant mixture consisting of 87.2 percent dichlorodifluoromethane (R-12) and 12.8 percent chlorodifluoromethane (R-22) were charged to a steel tube reactor. The refrigerant charge thus contained 11.6 g (0.13 moles) of R-22. 24.4 g or 1.43 moles of anhydrous liquid ammonia were added to the refrigerant mixture. The reactor tube was sealed and allowed to stand for 3 days at ambient temperature conditions. The composition was analyzed, and found to contain 99.754 percent R-12; 0.105 percent R-22, and a trace of other refrigerant (0.141 percent R-32). Analysis showed the reaction to be highly selective in destroying only R-22.

In order to recover substantially pure R-12 from the reaction mixture the ammonia in the reactor is converted to water soluble salts by the addition of dilute aqueous sulfuric acid solution. Because of the insolubility of the R-12 refrigerant in the aqueous salt solution, separate distinct phases form in the reactor consisting of a lower refrigerant phase and an upper aqueous phase. The lower refrigerant phase containing the R-12 can be withdrawn so it is substantially free of the water soluble salts.

EXAMPLE III

To demonstrate the effectiveness of other weak nitrogen-containing bases in dehalogenating halohydroalkanes the experiment of Example I was repeated using ethylenediamine in place of ammonia. Approximately 5.0 g of chlorodifluoromethane was mixed in the glass pressure tube with about 20 ml of ethylenediamine and allowed to warm to room temperature. A vigorous exothermic reaction ensued indicating weak nitrogen-containing bases other than anhydrous liquid ammonia will readily react with halohydroalkane refrigerant.

EXAMPLE IV

Dissolving metal reactions with ammonia or other weak base are useful in the destruction of most refrigerants, including the more stable perhalogenated types. Significantly reduced amounts of dissolving metals then previously required can be effectively used to achieve complete destruction of unwanted refrigerants. This can be shown by charging liquid ammonia to a reaction vessel and allowing it to cool by auto-refrigeration. When a temperature of $-10°$ to $-33°$ C. is reached 2 mol equivalents of calcium metal are added and stirred to give the typical blue solvated electron solution. Eight mole equivalents of dichlorodifluoromethane, about 4 times the amount of refrigerant then metal present to entirely dehalogenate the refrigerant, is allowed to react until the blue color no longer appears. The temperature of the reaction mixture is then allowed to rise. At about room temperature further destruction of the refrigerant occurs through reaction of only the remaining ammonia in the reactor.

EXAMPLE V

In order to dehalogenate CFCs and eliminate ammonium cyanide formed in the process 1 liter of anhydrous liquid ammonia is added with autochilling to a stainless steel reactor equipped with a stirrer, sight glasses and valves to permit addition and withdrawal of reactants, samples and products. These access means are at the top, bottom and middle sections of the reactor.

When ammonia addition is complete, the stirrer is actuated and 44 grams (1.1 moles) of calcium rod pieces are added through a lock-hopper at the top of the reactor. The deep blue color indicative of solvated electrons rapidly appears.

The refrigerant to be destroyed is then added below the surface of the liquid. 121 grams (1.0 moles) of R-12 dichlorodifluoromethane refrigerant are added to leave a slight excess of metal/electrons in the liquid. The reaction mixture is then allowed to warm. An exothermic reaction commences and cooling is started to maintain the temperature, and hence the pressure within the desired parameters of 50° to 80° F.

When the reaction ceases a sample of liquid is taken for refrigerant analysis. If the desired kill is achieved ammonia is withdrawn from the reactor as a vapor. When a dry cake of solid salts is all that remains 1 liter of 12 percent aqueous sodium hydroxide solution is added to convert the volatile ammonium salts to more stable sodium salts. The remaining slurry is discharged to a hydrolyzer tank where cyanide salts are converted to the corresponding formate salts. After this hydrolysis reaction is essentially complete, aqueous sodium hypochlorite or hydrogen peroxide is added to assure total destruction of cyanide compounds. The absence of cyanide is confirmed by spot test.

While the invention has been described in conjunction with specific examples thereof, they are illustrative only. Accordingly, many alternatives, modifications and variations will be apparent to persons skilled in the art in light of the foregoing description, and it is therefore intended to embrace all such alternatives, modifications and variations as to fall within the spirit and broad scope of the appended claims.

We claim:

1. A method of chemically dehalogenating a refrigerant which comprises the steps of:

(i) providing a halofluorohydrocarbon refrigerant;

(ii) reacting said halofluorohydrocarbon refrigerant with an ammonia or other nitrogen-containing base to dehalogenate said refrigerant, said reaction yielding a composition comprising a cyanide compound;

(iii) reacting said cyanide compound with a base selected from the group consisting of an alkali metal hydroxide and an alkaline earth metal hydroxide to provide a reaction mixture comprising a cyanide compound of said base, and (iv) hydrolyzing with water said cyanide compound of said base to yield a composition substantially free of said compound.

2. The method of claim 1 wherein said ammonia is anhydrous liquid ammonia.

3. The method of claim 1 wherein said nitrogen-containing base is a member selected from the group consisting of refrigerant soluble primary amines, secondary amines and tertiary amines.

4. The method of claim 2 wherein said halofluorohydrocarbon refrigerant is a chlorofluorohydrocarbon or bromofluorohydrocarbon, and the reaction of step (ii) yields a product comprising ammonium cyanide.

5. The method of claim 4 wherein the chlorofluorohydrocarbon and bromofluorohydrocarbon refrigerants are fluoromethane types selected from the group consisting of chlorodifluoromethane, fluorodichloromethane, chlorofluoromethane, bromofluoromethane, bromodifluoromethane, and mixtures thereof.

6. The method of claim 1 wherein said ammonia or other nitrogen-containing base is non-aqueous.

7. The method of claim 1 including the step of recovering ammonia for recycling.

8. The method of claim 1 wherein hydrolysis of the cyanide compound of said base yields an alkali metal formate.

9. A method of purifying a refrigerant composition, which comprises the steps of:

(i) providing a composition comprising at least two refrigerants, (a) a primary perhalogenated refrigerant compound and (b) a contaminating halofluorohydrocarbon refrigerant compound;

(ii) reacting the refrigerant composition of step (i) with a nitrogen-containing base to selectively decompose said contaminating halofluorohydrocarbon refrigerant compound (b) and yield a composition comprising said primary perhalogenated refrigerant compound and a cyanide compound;

(iii) reacting said cyanide compound of step (ii) with a base selected from the group consisting of an alkali metal hydroxide and an alkaline earth metal hydroxide to yield a reaction mixture comprising the primary perhalogenated refrigerant and a cyanide compound of said base;

(iv) hydrolyzing with water the cyanide compound of said base of step (iii) to form a useful product or a product of lesser toxicity, and (v) recovering said primary perhalogenated refrigerant sufficiently free of said contaminating halofluorohydrocarbon refrigerant to enable recycling/reuse.

10. The method of claim 9 wherein the nitrogen-containing base is a liquid ammonia or a member selected from the group consisting of refrigerant soluble primary amines, secondary amines and tertiary amines.

11. The method of claim 10 wherein the primary perhalogenated refrigerant compound (a) of step (i) is a halofluorocarbon compound selected from the group consisting of a chlorofluorocarbon and bromofluorocarbon.

12. The method of claim 11 wherein the contaminating halofluorohydrocarbon refrigerant compound (b) of step (i) is a chlorofluorohydrocarbon or a bromofluorohydrocarbon.

13. The method of claim 12 wherein the contaminating chlorofluorohydrocarbon and bromofluorohydrocarbon refrigerants are fluoromethane types selected from the group consisting of chlorodifluoromethane, fluorodichloromethane, chlorofluoromethane, bromofluoromethane, bromodifluoromethane, and mixtures thereof.

14. The method of claim 13 wherein the primary perhalogenated refrigerant compound is dichlorodifluoromethane.

15. The method of claim 9 wherein said refrigerant composition of step (i) comprises an azeotrope.

16. The method of claim 9 wherein said refrigerant composition of step (i) comprises a mixture of at least two refrigerants having substantially similar boiling points.

17. The method of claim 15 wherein the refrigerant composition of step (i) is an azeotrope comprising dichlorodifluoromethane and chlorodifluoromethane, and the recovered refrigerant of step (v) comprises dichlorodifluoromethane.

18. A method of dehalogenating refrigerants which comprises the steps of:

(i) providing a perhalogenated fluorocarbon refrigerant;

(ii) forming a solution of solvated electrons by dissolving a reactive metal in a solvent carrier of liquid ammonia or other nitrogen-containing base, said reactive metal being present in an amount sufficient to only partially dehalogenate said perhalogenated refrigerant;

(iii) reacting said refrigerant of step (i) with said solution of solvated electrons of step (ii) to yield a composition comprising a partially dehalogenated refrigerant carbanion;

(iv) allowing said refrigerant carbanion and any subsequent intermediates to react with said solvent carrier to complete the dehalogenation of said refrigerant and yield a reaction mixture comprising a cyanide compound;

(v) reacting said cyanide-containing reaction mixture of step (iv) with a metal hydroxide base to yield a reaction mixture comprising a cyanide compound of said base;

(vi) hydrolyzing with water the cyanide compound of said base of step (v) to form a useful product or a product of lesser toxicity.

19. The method of claim 18 wherein the solvated electrons of step (ii) are formed from a reactive metal selected from the group consisting of an alkali metal, alkaline earth metal, aluminum and mixtures thereof, and the solvent carrier is anhydrous liquid ammonia.

20. The method of claim 19 wherein said reactive metal is present in a sufficient amount to remove at least one but fewer than all of the halogens on said perfluorocarbon refrigerant.

21. The method of claim 19 wherein the solution of solvated electrons is formed with about 2 equivalents of reactive metal per mole of perhalogenated fluorocarbon refrigerant present.

22. The method of claim 19 wherein the reaction of step (iii) is conducted at temperatures sufficiently low as to retard reactions of the solvated electrons and anhydrous liquid ammonia with by-products of this reduction reaction.

23. The method of claim 19 wherein the perhalogenated fluorocarbon refrigerant of step (i) is a chlorofluorocarbon or a bromofluorocarbon.

24. The method of claim 19 wherein the perhalogenated fluorocarbon refrigerant is a member selected from the group consisting of chlorotrifluoromethane, bromotrifluoromethane, and fluorotrichloromethane.

25. The method of claim 24 wherein the perhalogenated fluorocarbon refrigerant of step (i) is dichlorodifluoromethane.

26. The method of claim 19 wherein the reaction mixture of step (iv) comprises ammonium cyanide which is converted to alkali metal cyanide by reacting with alkali metal hydroxide which in turn is hydrolyzed to an alkali metal formate.

* * * * *